(12) United States Patent
Sklar et al.

(10) Patent No.: US 7,083,647 B1
(45) Date of Patent: Aug. 1, 2006

(54) FIXATION SCREW, GRAFT LIGAMENT ANCHOR ASSEMBLY, AND METHOD FOR SECURING A GRAFT LIGAMENT IN A BONE TUNNEL

(76) Inventors: Joseph H. Sklar, 210 Park Dr., Longmeadow, MA (US) 01106; Charles L. Beck, Jr., 2318 Walker La., Salt Lake City, UT (US) 84117; Greta Jo Hays, 702 E. 1030 N., Logan, UT (US) 84341

( * ) Notice: Subject to any disclaimer, the term of this patent is extended or adjusted under 35 U.S.C. 154(b) by 0 days.

(21) Appl. No.: 09/715,714

(22) Filed: Nov. 17, 2000

Related U.S. Application Data

(63) Continuation-in-part of application No. 09/304,885, filed on May 4, 1999, now abandoned, which is a continuation-in-part of application No. 09/248,523, filed on Feb. 9, 1999, now Pat. No. 6,533,816, and a continuation-in-part of application No. 08/756,413, filed on Nov. 27, 1996, now Pat. No. 5,899,938.

(51) Int. Cl.
*A61F 2/08* (2006.01)

(52) U.S. Cl. ................ 623/13.14; 606/73; 411/424

(58) Field of Classification Search ........... 623/13.13, 623/13.11, 13.12, 13.15, 13.16, 13.17, 13.18; 606/63, 64, 72, 73; 411/398, 424
See application file for complete search history.

(56) References Cited

U.S. PATENT DOCUMENTS

| | | | |
|---|---|---|---|
| RE13,204 E | 2/1911 | Jossart | |
| 2,353,851 A | 7/1944 | Rosan | |
| 3,153,975 A | 10/1964 | Rapata | |
| 3,199,398 A | 8/1965 | Weisz | |
| 3,411,397 A | 11/1968 | Birmingham | |
| 3,516,324 A | 6/1970 | Berner | |
| 3,678,798 A | 7/1972 | Van Niel | |
| 3,731,724 A | 5/1973 | Dorflinger | |
| 3,765,295 A | 10/1973 | Ptak | |
| 3,942,407 A | 3/1976 | Mortensen | |
| 3,976,079 A | 8/1976 | Samuels et al. | |
| 4,083,289 A | 4/1978 | Erickson | |
| 4,085,651 A | 4/1978 | Koscik | |
| 4,407,618 A | 10/1983 | Kimura | |
| 4,484,570 A * | 11/1984 | Sutter et al. ............ 128/92 D |
| 4,535,925 A | 8/1985 | Ramey et al. | |
| 4,580,936 A | 4/1986 | Francis et al. | |
| 4,590,928 A | 5/1986 | Hunt et al. | |
| 4,708,132 A | 11/1987 | Silvestrini | |
| 4,716,893 A | 1/1988 | Fischer et al. | |
| 4,744,793 A | 5/1988 | Parr et al. | |
| 4,755,183 A | 7/1988 | Kenna | |
| 4,778,468 A | 10/1988 | Hunt et al. | |

(Continued)

FOREIGN PATENT DOCUMENTS

CA        1015989        8/1977

(Continued)

*Primary Examiner*—Bruce Snow
(74) *Attorney, Agent, or Firm*—Pandiscio & Pandiscio

(57) ABSTRACT

A fixation screw, graft ligament anchor assembly, and method for fastening a graft ligament in a bone tunnel. The screw comprises an elongated shank having a distal end and a proximal end, and a central axis extending from the distal end to the proximal end. Screw threads are disposed on the shank and extend from the distal end to the proximal end. The proximal end defines an end plane disposed transversely to the axis and at an angle thereto other than a normal angle.

17 Claims, 5 Drawing Sheets

U.S. PATENT DOCUMENTS

| | | |
|---|---|---|
| 4,784,126 A | 11/1988 | Hourahane |
| 4,828,562 A | 5/1989 | Kenna |
| 4,851,005 A | 7/1989 | Hunt et al. |
| 4,870,957 A | 10/1989 | Goble et al. |
| 4,927,421 A | 5/1990 | Goble et al. |
| 4,940,467 A | 7/1990 | Tronzo |
| 4,944,742 A | 7/1990 | Clemow et al. |
| 4,950,270 A | 8/1990 | Bowman et al. |
| 4,950,271 A | 8/1990 | Lewis et al. |
| 5,013,316 A | 5/1991 | Goble et al. |
| 5,037,422 A | 8/1991 | Hayhurst et al. |
| 5,062,843 A | 11/1991 | Mahony, III |
| 5,147,362 A | 9/1992 | Goble |
| 5,151,104 A | 9/1992 | Kenna |
| 5,152,790 A | 10/1992 | Rosenberg et al. |
| 5,211,647 A | 5/1993 | Schmieding |
| 5,234,430 A | 8/1993 | Huebner |
| 5,236,445 A | 8/1993 | Hayhurst et al. |
| 5,268,001 A | 12/1993 | Nicholson et al. |
| 5,282,802 A | 2/1994 | Mahony, III |
| 5,312,438 A | 5/1994 | Johnson |
| 5,324,308 A | 6/1994 | Pierce |
| 5,356,435 A | 10/1994 | Thein |
| 5,360,448 A | 11/1994 | Thramann |
| 5,376,119 A | 12/1994 | Zimmermann et al. |
| 5,383,878 A | 1/1995 | Roger et al. |
| 5,425,707 A | 6/1995 | Goldberg |
| 5,425,767 A | 6/1995 | Steininger et al. |
| 5,458,601 A | 10/1995 | Young, Jr. et al. |
| 5,470,334 A * | 11/1995 | Ross et al. .............. 606/72 |
| 5,632,748 A | 5/1997 | Beck, Jr. et al. |
| 5,645,589 A | 7/1997 | Li |
| 5,702,397 A | 12/1997 | Goble et al. |
| 5,707,395 A | 1/1998 | Li |
| 5,776,196 A | 7/1998 | Matsuzaki et al. |
| 5,899,938 A | 5/1999 | Sklar et al. |
| 5,906,632 A | 5/1999 | Bolton |
| 6,355,066 B1 | 3/2002 | Kim |
| 6,387,129 B1 * | 5/2002 | Rieser et al. ............ 623/13.14 |

FOREIGN PATENT DOCUMENTS

| | | |
|---|---|---|
| DE | 89 14 308 U1 | 3/1990 |
| EP | 0596177 B1 | 5/1994 |
| EP | 0834281 B1 | 4/1998 |
| FR | 2590792 | 6/1987 |
| FR | 2636835 | 3/1990 |
| JP | 5-300917 | 11/1993 |
| WO | WO 98/23229 A1 | 6/1998 |

* cited by examiner

FIXATION SCREW, GRAFT LIGAMENT ANCHOR ASSEMBLY, AND METHOD FOR SECURING A GRAFT LIGAMENT IN A BONE TUNNEL

REFERENCE TO RELATED APPLICATION

This is a continuation-in-part of (1) pending prior U.S. patent application Ser. No. 09/248,523, filed Feb. 9, 1999, now U.S. Pat. No. 6,533,816 by Joseph H. Sklar for GRAFT LIGAMENT ANCHOR AND METHOD FOR ATTACHING A GRAFT LIGAMENT TO A BONE; and (2) is a continuation in part of U.S. patent application Ser. No. 09/304,885, filed May 4, 1999 now abandoned by Joseph H. Sklar, Harold M. Martins and Richard F. Wenstrom, Jr. for GRAFT LIGAMENT ANCHOR AND METHOD FOR ATTACHING A GRAFT LIGAMENT TO A BONE, and is a continuation of U.S. patent application Ser. No. 08/756,413, filed Nov. 27, 1996 by Joseph H. Sklar, Harold M. Martins and Richard F. Wenstrom, Jr. for GRAFT LIGAMENT ANCHOR AND METHOD FOR ATTACHING A GRAFT LIGAMENT TO A BONE (now U.S. Pat. No. 5,899,938, issued May 4, 1999).

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support and/or retain organs in place within the body. Ligaments are typically composed of coarse bundles of dense white fibrous tissue which are disposed in a parallel or closely interlaced manner, with the fibrous tissue being pliant and flexible but not significantly extensible.

In many cases, ligaments are torn or ruptured as a result of accidents. Various procedures have been developed to repair or replace such damaged ligaments.

For example, in the human knee, the anterior and posterior cruciate ligaments (i.e., the "ACL" and "PCL") extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such procedures, bone tunnels are generally formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere in the patient; in other circumstances, the graft ligament may be a synthetic device. For the purposes of the present invention, all of the foregoing are collectively referred to as a "graft ligament".

It has been found that in securing graft tendons to tibias, because of the surface configuration of the tibia bone it often is necessary to advance a fixation screw well into a bone tunnel in the tibia, often so far that for one side of the screw to be substantially flush with the bone tunnel opening, the other side of the screw will have advanced past the outer dense hard cortical bone and entered the inner and softer cancellous bone.

It has further been found that to refrain from advancing the fixation screw to the aforementioned location (that is, to leave a portion of the screw in cortical bone all around the screw) requires that a proximal portion of the screw remain outside the bone tunnel and project from the tibia.

Thus, there is a need for a fixation screw, graft ligament anchor assembly and method which affords full advancement of a fixation screw, but at the same time permits the screw to be engaged all around in the cortical portion of the tibia or other bone.

OBJECTS OF THE INVENTION

An object of the invention is to provide a fixation screw configured for disposition in cortical bone portions, so as to strengthen the retention of the screw in the bone.

Another object of the invention is to provide a fixation screw which, when the screw is fully implanted, substantially conforms to a surrounding bone surface at a proximal end of the screw.

A further object of the invention is to provide a graft ligament anchor assembly for improved retention in a bone, such as a tibia, and which in operative position conforms to a surrounding bone surface.

A still further object is to provide a method for securing a graft ligament in a bone tunnel so as to improve retention of the graft ligament in the bone, and so as to provide for conformance of a graft ligament anchor and fixation screw to a surface of surrounding bone.

SUMMARY OF THE INVENTION

With the above and other objects in view, as will hereinafter appear, there is provided a fixation screw for fastening a graft ligament in a bone tunnel. The screw comprises an elongated shank having a distal end and a proximal end, and a central axis extending from the distal end to the proximal end. Screw threads are disposed on the shank and extend from the distal end to the proximal end. The proximal end defines an end plane disposed transversely to the axis and at an angle thereto other than a normal angle.

In accordance with a further feature of the invention there is provided a fixation screw comprising an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle.

In accordance with a further feature of the invention, there is provided a fixation screw for fastening a graft ligament in a bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning the end surface as generally a continuation of surrounding bone surface of a body in which the graft ligament is fastened.

In accordance with a further feature of the invention, there is provided a graft ligament anchor assembly comprising a tubular body having a bore therethrough, and proximal and distal ends. The tubular body is adapted for placement in a bone tunnel proximate an opening thereof in a bone surface. The tubular body comprises a deformable wall and defines, at least in part, a chamber for receiving a graft ligament therein. A fixation screw is provided for insertion into the tubular body axially of the tubular body, for impinging upon the deformable wall so as to press the deformable wall, and hence the graft ligament received in the chamber, toward a wall of the bore, to fix the graft ligament in the bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding bone surface of a body in which the graft ligament is fastened.

In accordance with a still further feature of the invention, there is provided a method for securing a graft ligament in a bone tunnel having an end opening in a bone surface, a free end of the graft ligament extending out of the bone tunnel end opening. The method comprises the steps of providing a fixation screw for insertion into the bone tunnel adjacent the graft ligament for impinging upon the graft ligament and a wall of the bone tunnel to fix the graft ligament in the bone tunnel. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding portions of the bone surface. The method further comprises the steps of pulling the graft ligament taut, inserting the screw into the bone tunnel and advancing the screw therein to threadedly engage the graft ligament and a wall of the bone tunnel to fix the graft ligament in the bone tunnel, and turning the screw until the shank proximal end surface thereof is substantially a continuation of the surrounding bone surface.

In accordance with another feature of the invention, there is provided a method for securing a graft ligament in a bone tunnel having an end opening in a bone surface, a free end of the graft ligament extending out of the bone tunnel end opening. The method comprises the step of providing a graft ligament anchor comprising a tubular body having a bore therethrough and proximal and distal ends, the tubular body comprising a deformable wall and defining at least in part a chamber, and a fixation screw. The screw comprises an elongated shank having a generally conically-shaped distal end portion, a proximal end, and a central axis extending from the distal end portion to the proximal end. Screw threads are disposed on the shank and extend from the distal end portion to the proximal end. The proximal end comprises a generally planar end surface disposed transversely to the axis and at an angle thereto other than a normal angle, and appropriate for positioning as generally a continuation of surrounding portions of the bone surface. The method includes the further steps of extending the graft ligament free end through the chamber, placing the tubular body in the end opening and in the bone tunnel, pulling the graft ligament taut, inserting the screw into the tubular body and advancing the screw therein to press the deformable wall, and hence the graft ligament received in the chamber, toward the wall of the bore, to fix the graft ligament in the bone tunnel, and turning the screw until the proximal end surface thereof is substantially a continuation of the bone surface therearound.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE PREFERRED EMBODIMENTS

Figure 1:
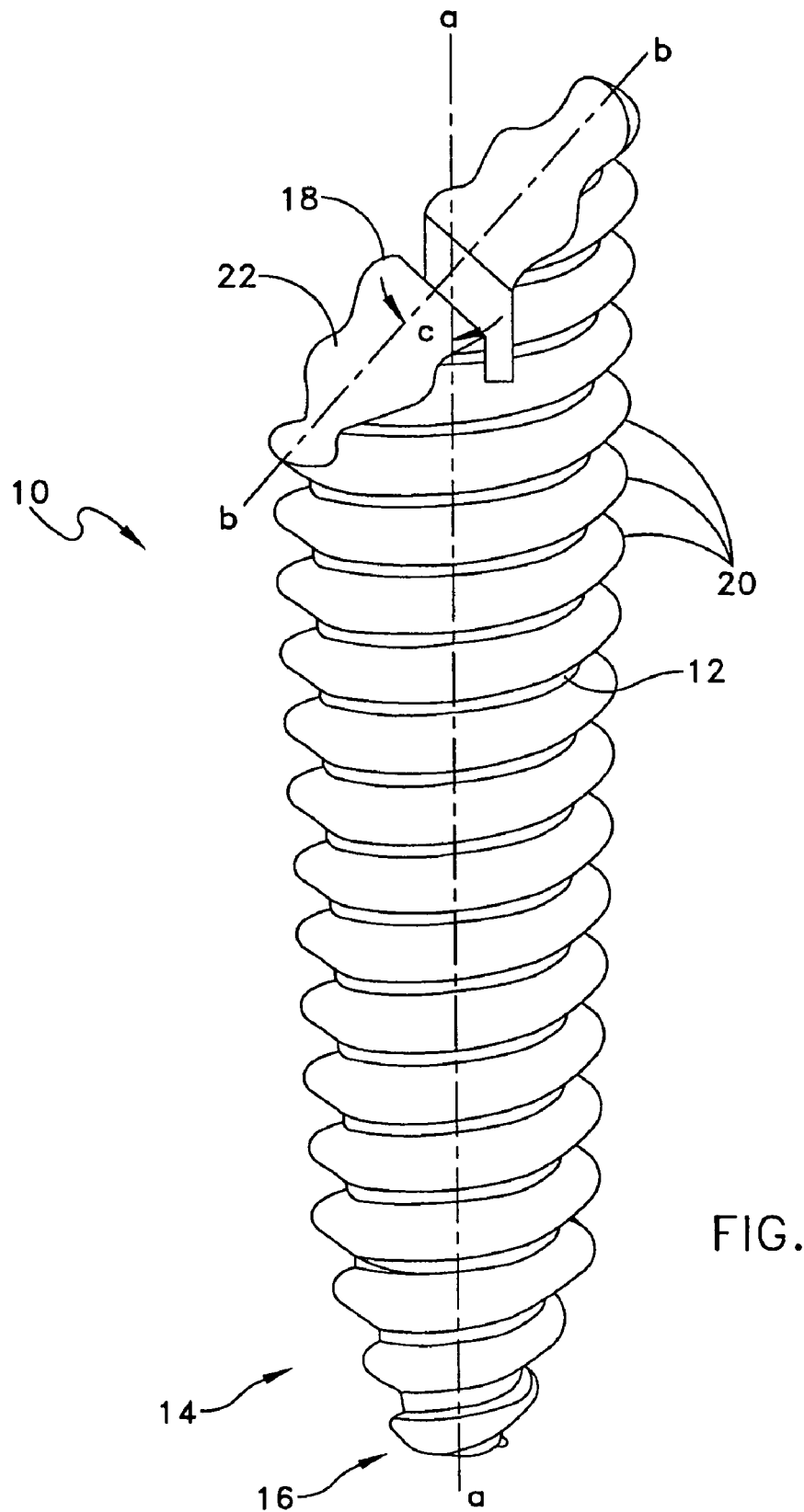
FIG. 1 is a perspective view of one form of a fixation screw for fastening a graft ligament in a bone tunnel, illustrative of an embodiment of the invention.

Referring to FIG. 1, it will be seen that an illustrative fixation screw 10 includes an elongated shank 12 having a distal end portion 14, which may be generally conically-shaped, as shown in FIG. 1, and have a generally pointed distal end 16. The shank 12 is further provided with a proximal end 18 defining an end plane b—b. A central axis a—a extends from the distal end 16 to the proximal end 18. The plane b—b is disposed transversely to the axis a—a and at an angle c thereto, the angle c being other than a normal angle, and preferably of about 40°–55°. The proximal end 18 may comprise a generally planar surface 22, as illustrated in FIG. 1. Screw threads 20 are disposed on the shank 12 and extend from the distal end 16 to the proximal end 18.

Figure 2:
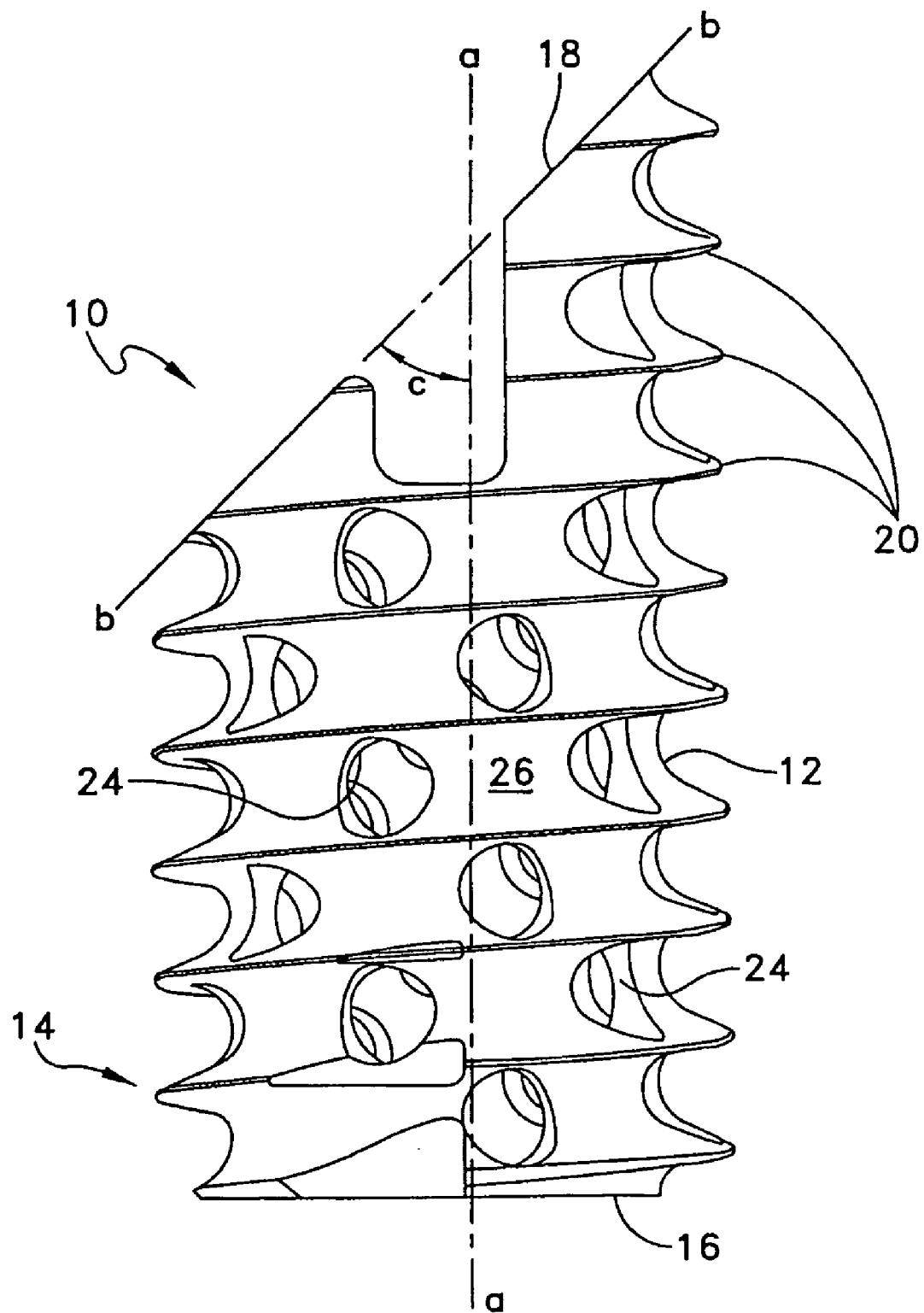
FIG. 2 is a side elevational view of an alternative embodiment of fixation screw.

Referring to FIG. 2, it will be seen that the fixation screw 10 may be of tubular structure and provided with apertures 24 extending through sidewalls 26 thereof, facilitating ingrowth of bone to further secure the screw in place over time. Further, as shown in FIG. 2, the distal end portion 14 of the screw 10 may be other than conical, such as generally cylindrical, and the distal end 16 of the screw 10 may be other than pointed, such as defining a plane normal to the axis a—a.

Figure 3:
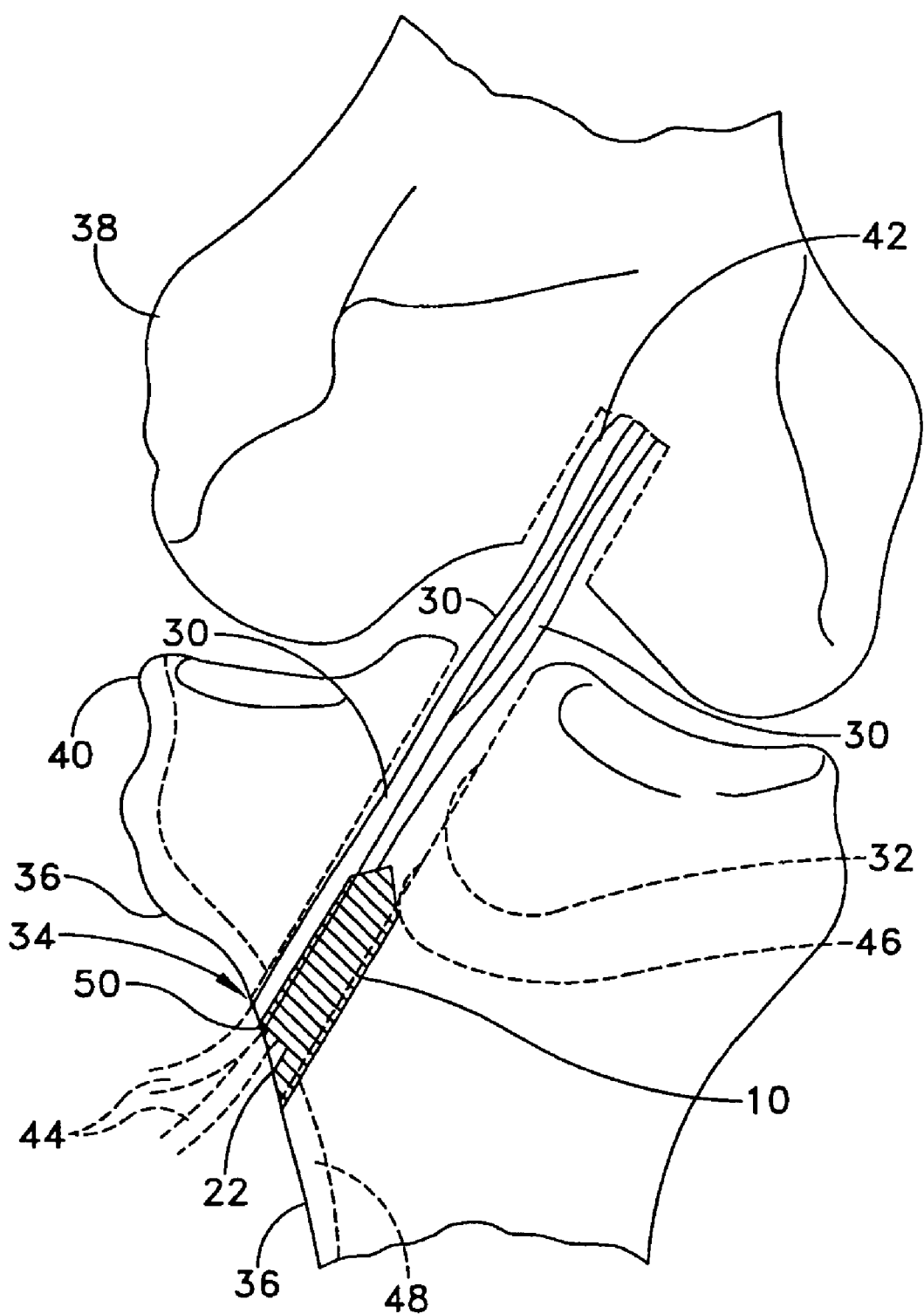
FIG. 3 is a diagrammatic illustration of the screw of FIG. 1 in operation.

In FIG. 3, there is illustrated a manner in which the fixation screw 10 of FIG. 1 or FIG. 2 may be used to secure a graft ligament 30 in a bone tunnel 32 having an end opening 34 in a bone surface 36. In FIG. 3, the bones shown for illustrative purposes are major bones of a knee joint, including a femur 38 and tibia 40. The invention presumes that one end 42 of the ligament 30 has been secured in the femur in accordance with known methods and that another end portion 44 extends from the end opening 34.

In the method illustrated in FIG. 3, an operator pulls the ligament 30 taut by manipulation of the exposed ligament end portion 44. The screw 10 is then inserted into the bone tunnel 32, by way of the end opening 34. The screw 10 is advanced into the bone tunnel 32, threadedly engaging the ligament 30 and a wall 46 of the bone tunnel 32, to secure the ligament 30 in the bone tunnel 32. As the screw 10 advances to nearly full insertion, the screw is turned until the shank proximal end surface 22 is disposed so as to be substantially flush with, and form substantially a continuation of, the surrounding bone surface 36.

Thus, threaded portions of the screw 10 are engaged throughout 360° with cortical portions 48 of the tibia 40, or other selected bone, to securely retain the screw in place. With the screw 10 in place, the exposed ligament end portions 44 may be snipped off along lines 50, shown in FIG. 3 (the "snipped off" portions of ligament end portions 44 are shown in phantom in FIG. 3). As noted above, when the embodiment of fixation screw shown in FIG. 2 is used, over time material from the bone wall 46 will migrate through the apertures 24, to further lock the screw in place.

Figure 4:
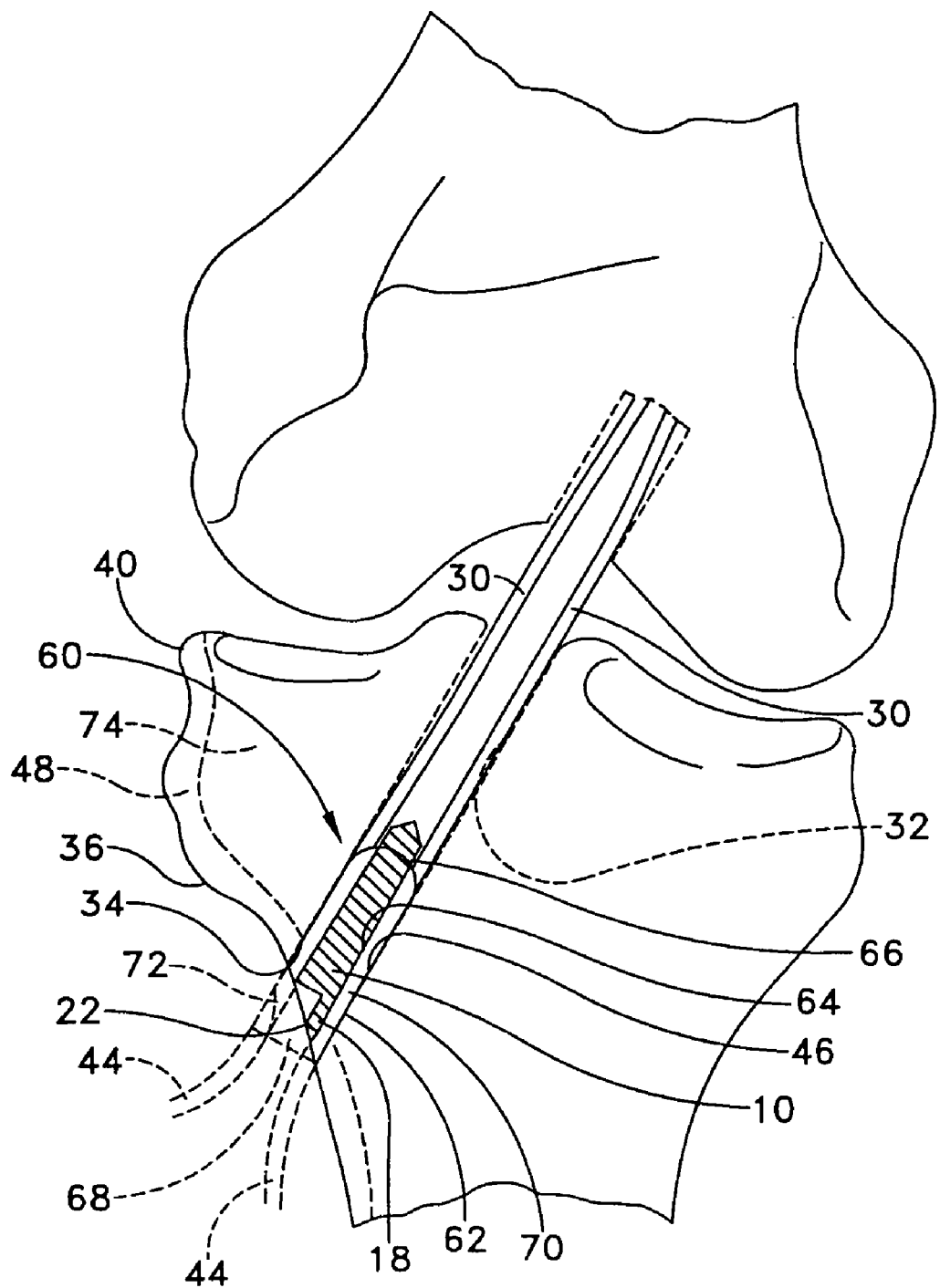
FIG. 4 is a diagrammatic illustration of a graft ligament anchor assembly including the screw of FIG. 1 and illustrating an anchor assembly in operation.

In FIG. 4, there is shown a graft ligament anchor 60 in a tibia 40. The anchor 60 includes the screw 10, as described hereinabove, and a tubular body 62 having a bore 64 therethrough and having distal and proximal ends 66, 68. The tubular body 62 is adapted for placement in the bone tunnel 32 proximate the end opening 34 thereof in the bone surface 36. A deformable wall 70 is disposed in the tubular body, defining at least in part a chamber 72 for receiving the graft ligament 30 therein.

In the anchor assembly 60 shown in FIG. 4, the tubular body 62 itself forms a deformable wall 70. In pending prior U.S. patent application Ser. No. 09/248,523, filed Feb. 9, 1999 by Joseph H. Sklar for GRAFT LIGAMENT ANCHOR AND METHOD FOR ATTACHING A GRAFT LIGAMENT TO A BONE, which pending prior patent application is hereby incorporated herein by reference, there are disclosed several ligament anchor assemblies having tubular bodies with alternative arrangements of deformable walls and appropriate for use in the anchor assembly presented herein.

In use of the graft ligament anchor assembly, the ligament end portions 44 are extended through the tubular body chamber 72 by an operator. The tubular body 62 is inserted in the end opening 34 of the bone tunnel 32. The ligament 30 is pulled taut by the operator. The fixation screw 10 is then inserted into the tubular body 62 and advanced to press the graft ligament 30 and deformable wall 70 toward the wall 46 of the bone tunnel 32, to fix the ligament to the bone tunnel wall 46. As the proximal end 18 of the screw 10 draws near the bone surface 36, the screw 10 is turned until the screw proximal end surface 22 is disposed so as to be flush with, and substantially a continuation of, the bone surface 36 therearound.

The tubular body 62 and the ligament end portions 44 may then be snipped off to provide a relatively smooth surface in the area of the closed opening 34 (the "snipped off" portions of tubular body 62 and the ligament end portions 44 are shown in phantom in FIG. 4).

In the embodiment shown in FIG. 4, the threads 20 of the screw 10 do not directly engage the cortical bone 48; however, the threads 20 force the tubular body 62 into engagement with the cortical bone 48, providing stronger fixation than if similarly engaged with a cancellous portion 74 of the bone 40.

There is thus provided an improved fixation screw, graft ligament anchor assembly and methods for fixing ligaments in bone tunnels.

In the aforementioned U.S. patent application Ser. No. 09/248,523, which patent application has already been incorporated herein by reference, there are also disclosed bone tunnel liners for lining the wall of a bone tunnel prior to securing a graft ligament therein.

Figure 5:
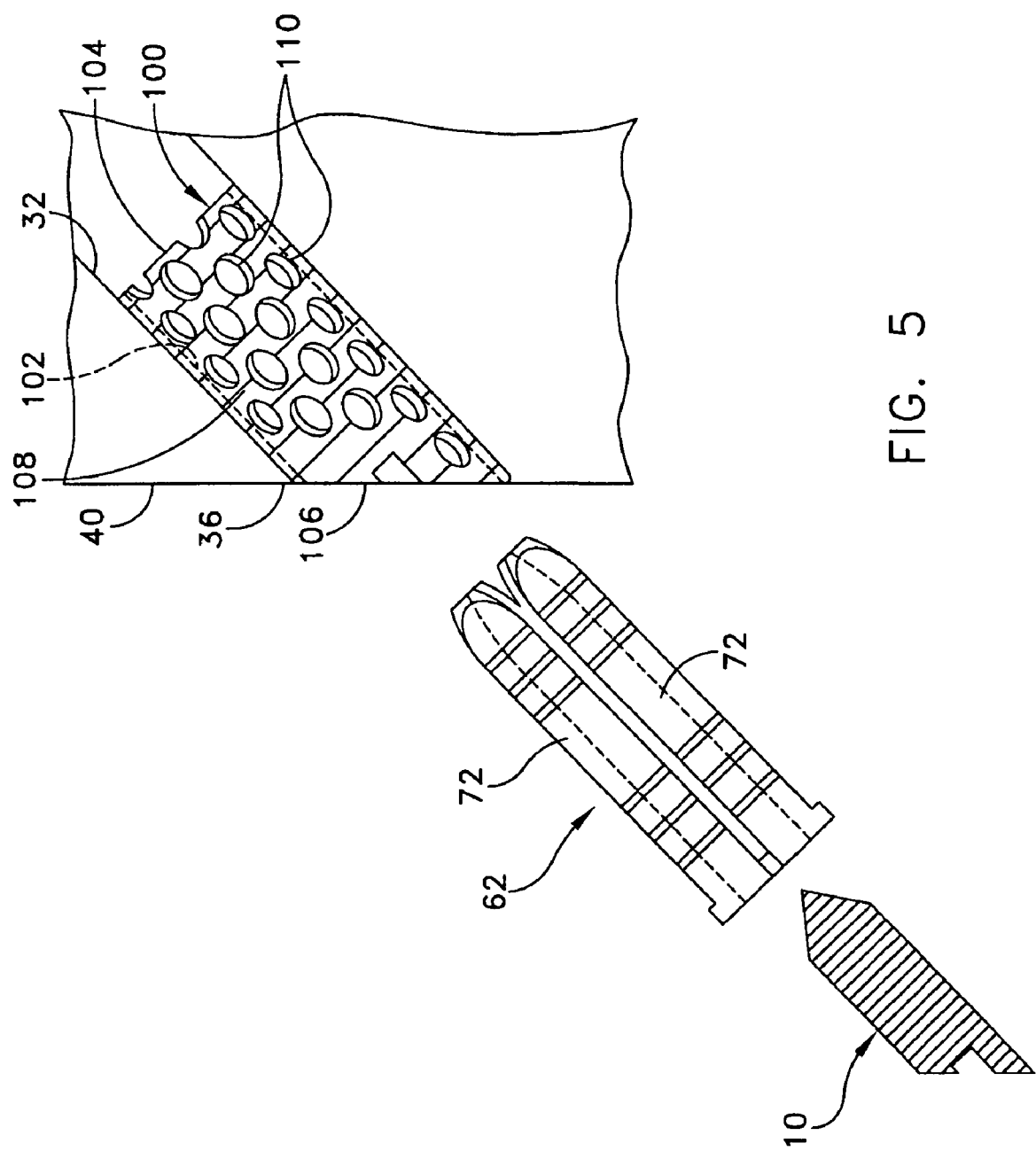
FIG. 5 is a diagrammatic illustration of still another embodiment of the present invention.

Looking now at FIG. 5, there is shown a bone tunnel liner 100 which may be positioned within a bone tunnel 32 of a bone 40. Bone tunnel liner 100 includes a central bore 102 extending from its distal end 104 to its proximal end 106. The outer surface of bone tunnel liner 100 includes screw threads 108 and preferably includes openings 110. In use, bone tunnel liner 100 is positioned in bone tunnel 32 in bone 40, the graft ligament's end portions are extended through chambers 72 of tubular body 62, tubular body 62 is inserted into bone tunnel liner 100, and fixation screw 10 is inserted into the central bore of tubular body 62 and advanced distally so as to press the tubular body's deformable walls, and hence the graft ligament, toward bone tunnel liner 100, whereby to secure the graft ligament in the bone tunnel.

In accordance with the present invention, the proximal end 106 of bone tunnel liner 100 is preferably formed with an end surface which is set at an angle to the longitudinal axis of the bone tunnel liner, whereby the proximal end of the bone tunnel liner may be disposed flush with, and substantially a continuation of, the bone surface 36 therearound.

It is to be understood that the present invention is by no means limited to the particular construction and method steps herein disclosed and/or shown in the drawings, but also comprises any modification or equivalent within the scope of the claims. For example, it will be apparent that the particular inclination of the proximal end plane to the shank central axis is selected to match the bone surface 36. The angle is determined by the application site morphology.

What is claimed is:

1. A fixation screw for fastening a graft ligament in a bone tunnel, the screw comprising:

an elongated shank having a distal end and a proximal end, and a central axis extending from the distal end to the proximal end; and screw threads disposed on said shank and extending from the distal end to the proximal end, said screw threads defining an outer periphery of said shank;

wherein the proximal end defines a generally planar end surface disposed transversely to the central axis and at an angle thereto other than a normal angle, and the planar end surface is formed so that the outer periphery of said shank is concentric with a maximum outer diameter of said screw threads;
wherein said shank is of tubular structure;
wherein said shank is provided with apertures in a sidewall thereof; and
wherein the shank distal end defines a plane normal to the shank central axis.

2. The fixation screw in accordance with claim 1 wherein the angle is about 40°–55°.

3. A fixation screw comprising an elongated shank having a distal end portion, a proximal end, and a central axis extending from the distal end portion to the proximal end, and screw threads disposed on said shank and extending from the distal end portion to the proximal end, said screw threads defining an outer periphery of said shank;
the proximal end comprising a generally planar end surface disposed transversely to the axis and at an angle thereto other than a normal angle, said planar end surface being formed so that the outer periphery of said shank is concentric with a maximum outer diameter of said screw thread;
wherein said shank is of tubular structure;
wherein said shank is provided with apertures in a sidewall thereof; and
wherein the shank distal end defines a plane normal to the shank central axis.

4. The fixation screw in accordance with claim 3 wherein the angle is about 40°–55°.

5. A fixation screw for fastening a graft ligament in a bone tunnel, said screw comprising:
an elongated tubular shank having:
a distal end portion;
a proximal end;
a central axis extending from the distal end portion to the proximal end; and
screw threads disposed on said shank and extending from the distal end portion to the proximal end, the screw threads defining an outer periphery of said shank;
the proximal end comprising no more than one planar and generally annular end surface entirely disposed in a single plane extending transversely to the central axis and at an angle thereto other than a normal angle, said shank being provided with apertures in a sidewall thereof; and the end surface being configured such that the outer periphery of said shank is concentric with a maximum outer diameter of said screw threads, and the end surface is adapted for positioning as generally a continuation of surrounding bone surface of a body in which the graft ligament is fastened, and the shank distal end portion defines a plane normal to the shank central axis.

6. The fixation screw in accordance with claim 5 wherein the angle is about 40°–55°.

7. A graft ligament anchor assembly comprising:
a tubular body having a bore therethrough and proximal and distal ends, said tubular body being adapted for placement in a bone tunnel proximate an opening thereof in a bone surface;
said tubular body comprising a deformable wall defining at least in part a chamber for receiving a graft ligament therein; and
a fixation screw for insertion into said tubular body axially of said tubular body, for impinging upon said deformable wall so as to press said deformable wall, and hence the graft ligament received in the chamber, toward a wall of the bone tunnel, to fix the graft ligament in the bone tunnel, said screw comprising:
an elongated shank having
a distal end portion;
a proximal end;
a central axis extending from the distal end portion to the proximal end; and
screw threads disposed on said shank and extending from the distal end portion to the proximal end; and
the proximal end comprising a generally planar end surface disposed transversely to the axis and at an angle thereto other than a normal angle and appropriate for positioning as generally a continuation of surrounding bone surface of a body in which the graft ligament is fastened.

8. The anchor assembly in accordance with claim 7 wherein said screw shank is of a tubular structure.

9. The fixation screw in accordance with claim 8 wherein said screw shank is provided with apertures in a sidewall thereof.

10. The fixation screw in accordance with claim 9 wherein the shank distal end defines a plane normal to the shank central axis.

11. The fixation screw in accordance with claim 7 wherein the distal end portion is generally conically-shaped.

12. The fixation screw in accordance with claim 7 wherein the angle is about 40°–55°.

13. A fixation screw for fastening a graft ligament in a bone tunnel, the screw comprising:
an elongated shank having a distal end and a proximal end, and a central axis extending from the distal end to the proximal end;
screw threads disposed on said shank and extending from the distal end to the proximal end, said screw threads defining an outer periphery of said shank;
wherein the proximal end defines a generally planar end surface disposed transversely to the central axis and at an angle thereto other than a normal angle, and the planar end surface is formed so that the outer periphery of said shank is concentric with a maximum outer diameter of said screw threads;
wherein said shank is of a tubular structure;
wherein said shank is provided with apertures in a sidewall thereof; and
wherein the shank distal end defines a plane normal to the shank central axis.

14. A fixation screw for fastening a graft ligament in a bone tunnel, the screw comprising:
an elongated shank having a distal end and a proximal end, and a central axis extending from the distal end to the proximal end;
screw threads disposed on said shank and extending from the distal end to the proximal end, said screw threads defining an outer periphery of said shank;
wherein the proximal end defines no more than one planar and generally annular end surface entirely disposed in a single plane extending transversely to the central axis and at an angle thereto other than a normal angle, and the planar end surface is formed so that the outer periphery of said shank is concentric with a maximum outer diameter of said screw threads; and
wherein said shank is of tubular structure and is provided with apertures in a sidewall thereof; and
wherein the shank distal end defines a plane normal to the shank central axis.

15. A fixation screw for fastening a graft ligament in a bone tunnel, the screw comprising:

an elongated shank having a distal end and a proximal end, and a central axis extending from the distal end to the proximal end;

screw threads disposed on said shank and extending from the distal end to the proximal end, said screw threads defining an outer periphery of said shank;

wherein the proximal end defines a generally planar end surface disposed transversely to the central axis and at an angle thereto other than a normal angle, and the planar end surface is formed so that the outer periphery of said shank is concentric with a maximum outer diameter of said screw threads;

wherein said shank is of tubular structure;

wherein said shank is provided with apertures in a sidewall thereof; and wherein the shank distal end defines a plane normal to the shank central axis.

16. A fixation screw comprising:

an elongated shank having:
   a distal end portion;
   a proximal end;
   a central axis extending from the distal end portion to the proximal end; and screw threads disposed on said shank and extending from the distal end portion to the proximal end, said screw threads defining an outer periphery of said shank;

the proximal end comprising no more than one planar and generally annular end surface entirely disposed in a single plane extending transversely to the axis and at an angle thereto other than a normal angle, and said end surface is formed so that the outer periphery of said shank is concentric with a maximum outer diameter of said screw threads;

wherein said shank is of tubular structure;

wherein said shank is provided with apertures in a sidewall thereof; and wherein the shank distal end defines a plane normal to the shank central axis.

17. A fixation screw comprising:

an elongated shank having:
   a distal end portion;
   a proximal end;
   a central axis extending from the distal end portion to the proximal end; and screw threads disposed on said shank and extending from the distal end portion to the proximal end, said screw threads defining an outer periphery of said shank;

the proximal end comprising a generally planar end surface disposed transversely to the axis and at an angle thereto other than a normal angle, and said planar end surface is formed so that the outer periphery of said shank is concentric with a maximum outer diameter of said screw threads;

wherein said shank is of tubular structure;

wherein said shank is provided with apertures in a sidewall thereof; and wherein the shank distal end defines a plane normal to the shank central axis.

* * * * *